(12) United States Patent
Sims et al.

(10) Patent No.: US 8,732,935 B2
(45) Date of Patent: May 27, 2014

(54) STENT-GRAFT WITH PROXIMAL AND DISTAL ATTACHMENT, DELIVERY CATHETER AND METHODS OF MAKING SAME

(75) Inventors: Daniel D. Sims, San Antonio, TX (US); Jeffrey N. Steinmetz, Arvada, CO (US); Conor P. Mullens, San Antonio, TX (US)

(73) Assignee: Advanced Bio Prosthetic Surfaces, Ltd., a wholly owned subsidiary of Palmaz Scientific, Inc., Dallas, TX (US)

( * ) Notice: Subject to any disclaimer, the term of this patent is extended or adjusted under 35 U.S.C. 154(b) by 0 days.

(21) Appl. No.: 13/445,131

(22) Filed: Apr. 12, 2012

(65) Prior Publication Data

US 2012/0197381 A1 Aug. 2, 2012

Related U.S. Application Data

(62) Division of application No. 11/215,984, filed on Aug. 31, 2005, now Pat. No. 8,187,318.

(51) Int. Cl.
| | |
|---|---|
| *B23P 13/04* | (2006.01) |
| *A61F 2/95* | (2013.01) |
| *A61F 2/966* | (2013.01) |
| *A61F 2/91* | (2013.01) |
| *A61F 2/07* | (2013.01) |

(52) U.S. Cl.
CPC ... *A61F 2/95* (2013.01); *A61F 2/91* (2013.01); *A61F 2/07* (2013.01); *A61F 2002/075* (2013.01); *A61F 2/966* (2013.01); *A61F 2240/001* (2013.01)
USPC ...................... 29/525.01; 623/1.11

(58) Field of Classification Search
USPC .............. 29/527.1, 525.14, 525.13, 469, 506, 29/428; 623/1.11, 1.15, 1.16, 1.1, 1.44, 623/1.2, 1.19, 1.35; 141/2; 219/609, 219/615–618
See application file for complete search history.

(56) References Cited

U.S. PATENT DOCUMENTS

| | | | |
|---|---|---|---|
| 4,416,028 A | 11/1983 | Eriksson et al. ................... 3/1.4 |
| 4,731,073 A | 3/1988 | Robinson .......................... 623/1 |
| 4,816,339 A | 3/1989 | Tu et al. ........................ 428/421 |
| 4,955,899 A | 9/1990 | Della Corna et al. ............. 623/1 |
| 4,969,896 A | 11/1990 | Shors ................................ 623/1 |
| 5,084,065 A | 1/1992 | Weldon et al. ..................... 623/1 |
| 5,102,417 A | 4/1992 | Palmaz ........................ 606/195 |
| 5,334,201 A | 8/1994 | Cowan .............................. 623/1 |
| 5,630,840 A | 5/1997 | Mayer ............................... 623/1 |
| 5,667,523 A | 9/1997 | Bynon et al. ................... 606/198 |
| 5,674,241 A | 10/1997 | Bley et al. ...................... 606/198 |
| 5,695,517 A | 12/1997 | Marin et al. ................... 606/198 |
| 5,735,892 A | 4/1998 | Myers et al. ...................... 623/1 |
| 5,800,517 A | 9/1998 | Anderson et al. ............. 623/1.11 |
| 5,824,045 A | 10/1998 | Alt .................................... 623/1 |

(Continued)

FOREIGN PATENT DOCUMENTS

| | | | |
|---|---|---|---|
| DE | 3918736 | 12/1990 | ............... A61F 2/06 |
| EP | 0 960 607 | 12/1999 | ............... A61F 2/06 |
| WO | 03/013337 | 2/2003 | |

*Primary Examiner* — John C Hong
(74) *Attorney, Agent, or Firm* — J. Peter Paredes; Rosenbaum IP

(57) ABSTRACT

A metallic or pseudometallic covered stent in which the stent component and the cover component are each fabricated of biocompatible metallic or pseudometallic materials, in which the cover and the stent are joined by at least one juncture at each of a proximal and distal end of the stent and the cover. A method of joining the stent and the cover is also disclosed.

10 Claims, 6 Drawing Sheets

(56) References Cited

U.S. PATENT DOCUMENTS

| | | | |
|---|---|---|---|
| 5,954,764 A | 9/1999 | Parodi | 623/1 |
| 6,123,723 A | 9/2000 | Konya et al. | 623/1.11 |
| 6,124,523 A | 9/2000 | Banas et al. | 623/11 |
| 6,179,878 B1 | 1/2001 | Duerig et al. | 623/902 |
| 6,214,039 B1 | 4/2001 | Banas et al. | 623/1.13 |
| 6,254,632 B1 | 7/2001 | Wu et al. | 623/1.15 |
| 6,322,585 B1 | 11/2001 | Khosravi et al. | 623/1.11 |
| 6,413,269 B1 | 7/2002 | Bui et al. | 623/1.11 |
| 6,451,052 B1 | 9/2002 | Burmeister et al. | 623/1.16 |
| 6,699,277 B1 | 3/2004 | Freidberg et al. | 623/1.13 |
| 6,800,089 B1 | 10/2004 | Wang | 623/1.44 |
| 7,300,457 B2 | 11/2007 | Palmaz | 623/1.13 |
| 2003/0130718 A1 | 7/2003 | Palmas et al. | 623/1.12 |
| 2004/0093066 A1 | 5/2004 | Durcan | 623/1.15 |
| 2004/0098094 A1 | 5/2004 | Boyle et al. | 623/1.13 |
| 2004/0186550 A1 | 9/2004 | Bonsignore | 623/1.15 |
| 2006/0259131 A1 | 11/2006 | Molaei et al. | 623/1.44 |
| 2007/0112415 A1 | 5/2007 | Bartlett | 623/1.15 |

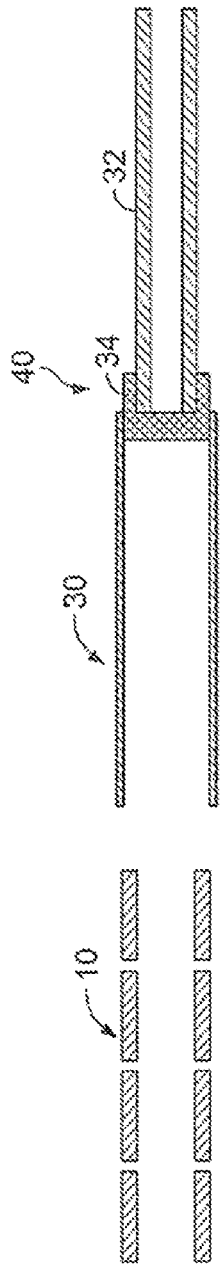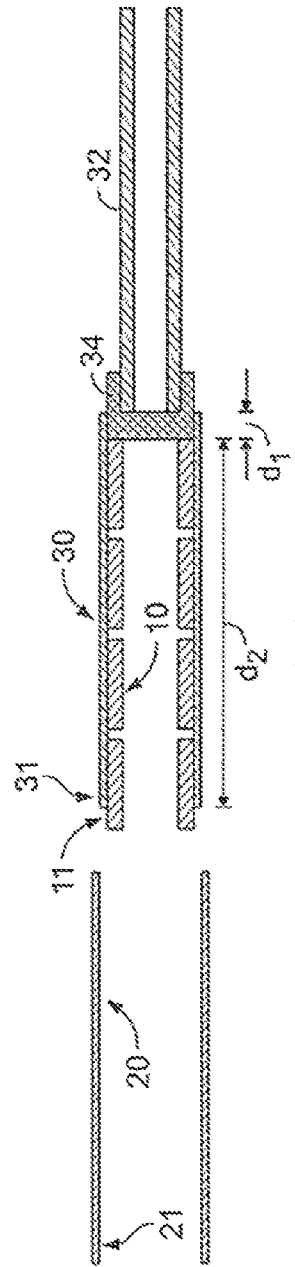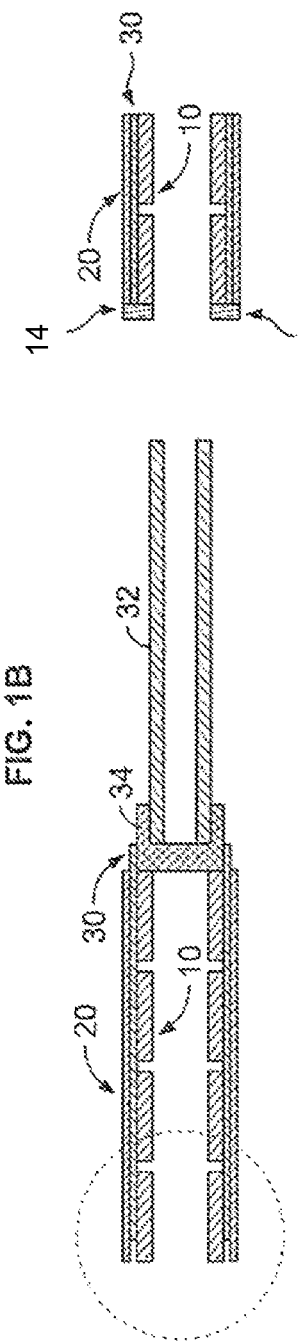

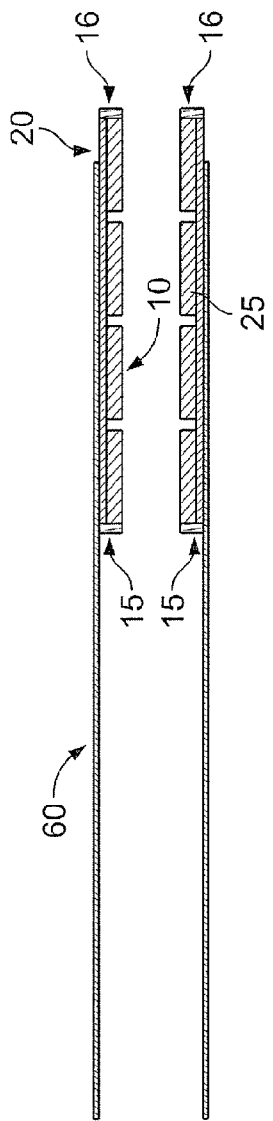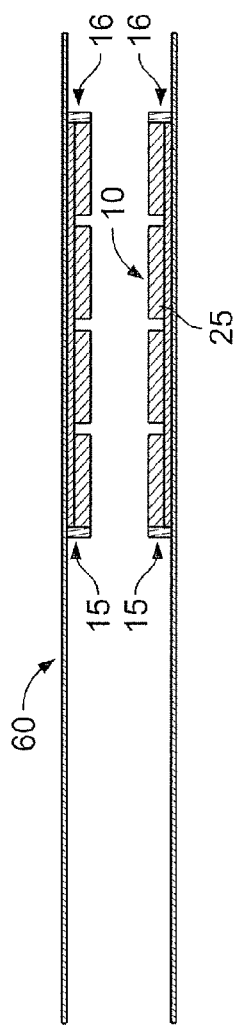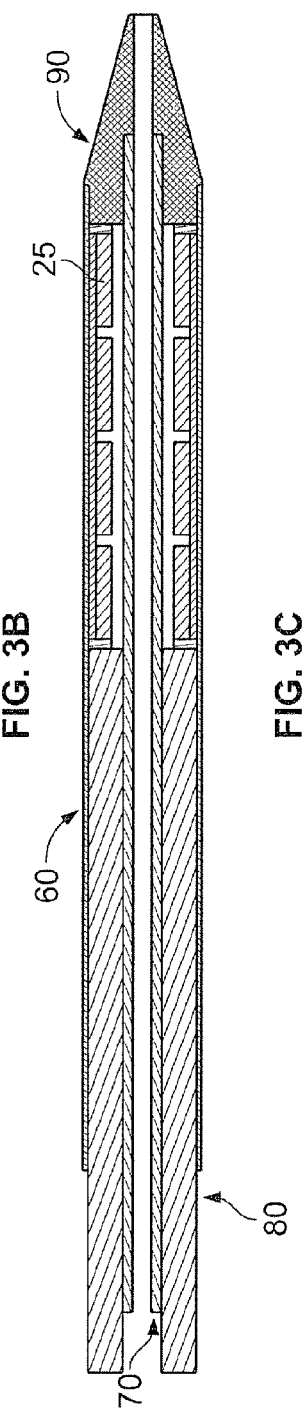

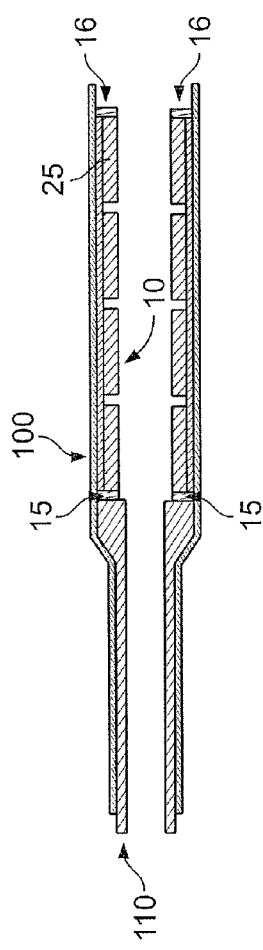
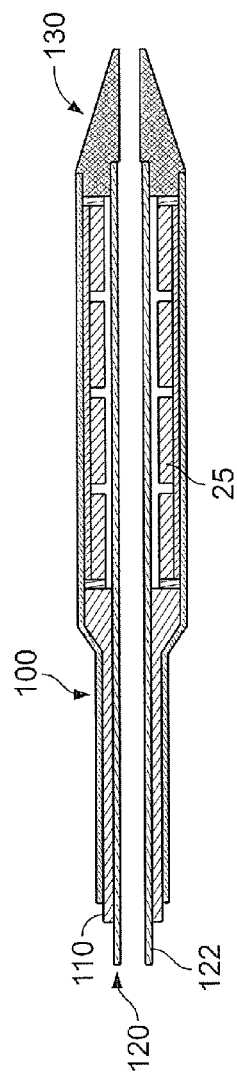
FIG. 5A
FIG. 5B

STENT-GRAFT WITH PROXIMAL AND DISTAL ATTACHMENT, DELIVERY CATHETER AND METHODS OF MAKING SAME

CROSS-REFERENCE TO RELATED APPLICATIONS

The present invention claims priority, as a divisional application, to U.S. patent application Ser. No. 11/215,984, which was filed on Aug. 31, 2005, and the aforementioned patent application is incorporated by reference in its entirety.

BACKGROUND OF THE INVENTION

The present invention pertains generally to implantable medical devices and, more particularly, to implantable medical devices which are capable of being implanted utilizing minimally-invasive delivery techniques. More particularly, the present invention relates to covered stents, stent-grafts and stent-graft-type devices that are implanted into anatomical passageways using minimally invasive delivery techniques. More specifically, the present invention comprises covered stents, stent-grafts and stent-graft-type devices that are fabricated entirely of biocompatible metals or of biocompatible materials which exhibit biological response and material characteristics substantially the same as biocompatible metals, such as for example composite materials (hereinafter referred to as "pseudometals" or by the property of being "pseudometallic"). Most specifically, the present invention relates to metal stents and metal stent covers wherein the metal stent cover is attached by at least one juncture between the metal stent at each of proximal and distal ends thereof.

Stents are typically lattice structures capable of adopting both a diametrically compressed configuration, for delivery to the site of deployment, and a diametrically expanded configuration, in which the stent presses outward and against the inner wall of the anatomical passageway to provide structural support to the vessel, restore and maintain vascular patency. Endoluminal stents, for example, are frequently used post-angioplasty to provide a structural support for a blood vessel and reduce the incidence of restenosis following percutaneous balloon angioplasty. For example, endovascular stents may be introduced to a site of disease or trauma within the body's vasculature from an introductory location remote from the disease or trauma site using an introductory catheter, passed through the vasculature communicating between the remote introductory location and the disease or trauma site, and released from the introductory catheter at the disease or trauma site to maintain patency of the blood vessel at the site of disease or trauma.

In many applications, it is desirable to provide a stent with a covering capable of conferring particularly desirable properties that the stent alone does not possess. For example, bare stents have been associated with significant restenosis rates and, due to the typically large fenestrations in the walls of the stent required to accommodate stent expansion from the compressed to the expanded diametric stage, permit particulate material, such as fragmented plaque, to pass from the vessel wall into the bloodstream. The relatively large fenestrations permit particulate material resident on the vascular walls, such as friable plaque or embolic material, to pass through the fenestrations and into the general circulation. Such undesirable effects may be reduced, however, by providing the stent with a covering over either the luminal or abluminal surfaces, or both surfaces, thereby forming a covered-stent or for purposes of this application, synonymously, a stent-graft.

SUMMARY OF THE INVENTION

In accordance with the present invention, a covered stent having proximal and distal affixation points between the stent and the cover components is provided.

Additionally, a method of attaching the cover to the stent is provided in which the stent is loaded into a restraining sheath having a pusher assembly concentrically engaged in the restraining sheath; the stent is loaded to a depth within the restraining sheath which permits the proximal end of the stent to remain exposed from the end of the restraining sheath; the cover is concentrically engaged about the outer circumference of the restraining sheath and aligned such that the proximal end of the cover is in concentric alignment with the proximal end of the stent; a proximal affixation is created between the proximal end of the stent and the proximal end of the cover; the restraining sheath is then positioned in co-axial alignment with a distal end of a constraining tube, and the pusher assembly actuated to push the stent and the proximally affixed cover into the distal end of the constraining tube to a point where the distal end of the stent and the distal end of the cover are exposed; a distal affixation is created between the distal end of the stent and the distal end of the cover, and the now proximally and distally affixed stent and cover are passivated and subsequently positioned in co-axial alignment with a distal end of a constraining tube, and a pusher assembly actuated to push the stent and the proximally affixed cover into the distal end of the delivery catheter lumen; a pusher assembly is then loaded into the delivery catheter from the proximal end of the catheter, and a guidewire and atraumatic tip is loaded in retrograde fashion from the distal end of the delivery catheter.

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

BRIEF DESCRIPTION OF THE DRAWINGS

FIGS. 1A-1D present sequential side-elevational cross-sectional views depicting a loading assembly in accordance with an inventive apparatus and method for preparing a proximally-joined covered stent assembly.

FIGS. 3A-3C presents sequential side-elevational cross-sectional views depicting loading of the inventive proximally and distally-joined covered stent assembly into a delivery catheter.

FIGS. 5A-5B presents sequential side-elevational cross-sectional views depicting catheter assembly in accordance with the alternative preferred embodiment of the present invention.

DETAILED DESCRIPTION OF THE INVENTION

Figure 2A:
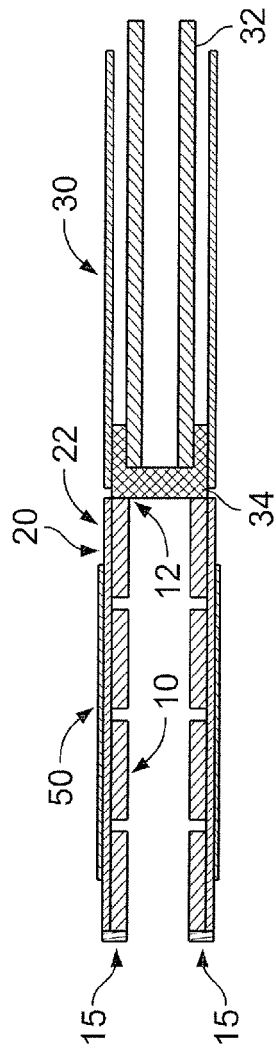
FIGS. 2A-2B present sequential side-elevational cross-sectional views of a transfer assembly in accordance with the inventive apparatus and method for preparing a proximally- and distally-joined covered stent assembly.

Turning now to the accompanying figures, FIGS. 1A-1D depict the preparation of a proximally-joined covered stent using a loading/welding fixture 40. FIG. 1A depicts the loading of stent 10 into the lumen of loading sheath 30 of loading/welding fixture 40. Loading/welding fixture 40 consists generally of the cylindrical loading sheath 30 and a pusher rod 32 having an abutment member 34 coupled to one end of the pusher rod 32. The abutment member 34 is concentrically engaged within the lumen of loading sheath 30 and is capable of reciprocal movement therein. The abutment member 34 and pusher rod 32 serve dual functions: first, the abutment member 34 acts as a stop during insertion of the stent 10 into the lumen of the loading sheath 30 to properly position the stent 10 therein, and second, the pusher rod 32 and abutment member 34 act to eject the proximally-affixed stent and cover from the lumen of the loading sheath 30.

FIG. 1B depicts the loading of cover 20 over an abluminal surface of the loading sheath 30. As is shown in FIG. 1B, abutment member 34 is positioned within the lumen of loading sheath 30 a distance d2, such that the remaining opening of the lumen of loading sheath 30 has a length of d1. Length d1 also corresponds to the degree of overhang or exposure of stent 10 from the proximal end region 31 of loading sheath 30 that is required for affixation of the cover 20 to the stent 10. The cover 20 is concentrically positioned over the abluminal surface of the loading sheath 30 and a proximal end of the cover 20 is aligned with the proximal end of the stent 10, such that the loading sheath 30 is positioned intermediate the stent 10 and the cover 20, with the exposed proximal end 11 of the stent 10 and the proximal end 21 of the cover 20 being in adjacent proximity therebetween. Therefore, as shown in the circled portion of FIG. 1C, after cover 20 has been loaded over loading sheath 30, the proximal end region 11 of stent 10 and proximal end region 21 of cover 20 may be joined without interference from proximal end region 31 of loading sheath 30. FIG. 1D depicts an exploded view of the circled region of FIG. 1C, with an example of such a join between proximal end region 11 of stent 10 and proximal end region 21 of cover 20 shown by solid box 14. Thus FIG. 1D depicts a proximally-joined covered stent assembly comprising stent 10 contained within cover 20 with a joining point 15 between the proximal end regions 11 and 21 of stent 10 and cover 20.

Figure 2B:
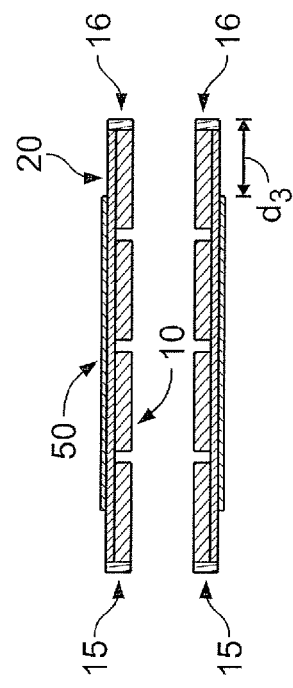

FIGS. 2A-2B depict loading the proximally joined stent 10 and cover 20 into a constraining tube 50 and the subsequent formation of a distal juncture 16 between the distal end 12 of stent 10 and the distal end 22 of cover 20. FIG. 2A depicts a proximally-joined covered stent assembly prepared as in FIG. 1, which has been ejected from the loading sheath 30 by axial movement of the pusher rod 32 and the abutment member 34 within the loading sheath 30. By bringing a constraining tube 50 into co-axial alignment with the loading sheath 30, as the proximally-joined covered stent assembly is ejected from the loading sheath 30, it is pushed into the constraining tube 50. The proximally-joined covered stent assembly is positioned in the constraining tube 50 such that the assembly extends and is exposed from the distal end of the constraining tube 50 a distance $d_3$. The exposed distal end of the assembly permits formation of a distal junction 16 between the stent 10 and the cover 20.

FIGS. 3A-3C depict the preparation of an assembly comprising a catheter sheath 60, a proximally- and distally-joined covered stent 25, a pusher member 80, a guidewire shaft 70 and an atraumatic tip 90. In FIG. 3A, a proximally- and distally-joined covered stent assembly is partially contained within a catheter sheath 60. The proximally- and distally-joined covered stent assembly 25 of FIG. 3A may be obtained as shown in FIGS. 1 and 2. In FIG. 3B, the proximally- and distally-joined covered stent assembly of FIG. 3A has been pushed completely within catheter sheath 60, while in FIG. 3C a guidewire shaft 70 is co-axially inserted through the central lumen of the covered stent assembly 25 and extends beyond the terminal (proximal) end of the pusher member 80 and the catheter sheath 60. An atraumatic tip 90 is affixed to a distal end of the guidewire shaft 70 prior to insertion of the guidewire shaft 70. The atraumatic tip 90 is refracted into abutting relation with a distal end of the catheter sheath 60, thereby enclosing the covered stent assembly 25 within the catheter sheath 60.

In accordance with the best mode for practicing the invention, cover 20 is preferably in its martensitic state and unstrained at room temperature, when positioned on the loading sheath 30. The stent 10, however, is preferably austenitic and should be loaded into the loading sheath 30 in the presence of a cooling medium, e.g., liquid nitrogen bath, dry ice and alcohol bath, flow of chilled gas, etc. The stent in its compressed diameter is strained, thus, in order to operate the other manipulative steps, needs to be within the constraining tube 50 or the catheter tube. The protruding proximal or distal ends of the stent will, however, flare slightly as they are exposed to room temperatures after being loaded into the loading sheath 30 and the constraining tube 50. This very slight flare, however, ensures good apposition between the stent 10 and cover 20 and facilitates forming a junction between the stent 10 and the cover 20, such as by resistance spot welding.

Figure 4A:
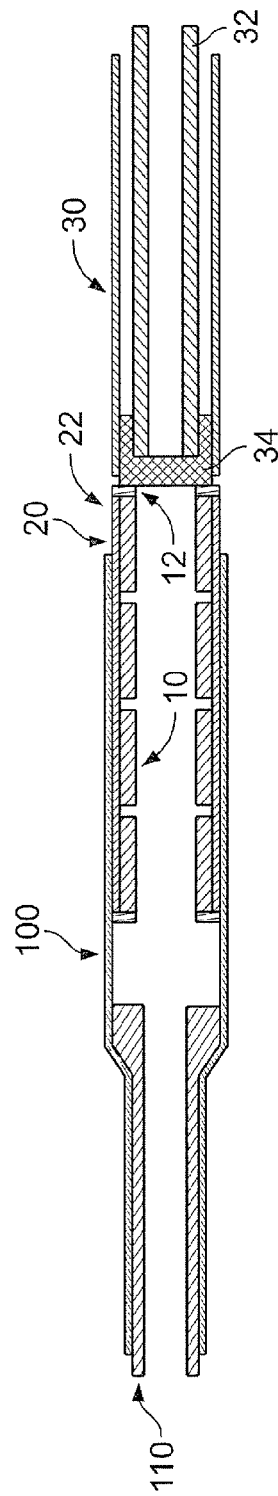
FIGS. 4A-4B presents sequential side-elevational cross-sectional views depicting loading of a proximally- and distally-joined covered stent assembly into a tapered catheter sheath in accordance with an alternative preferred embodiment of the present invention.
Figure 4B:
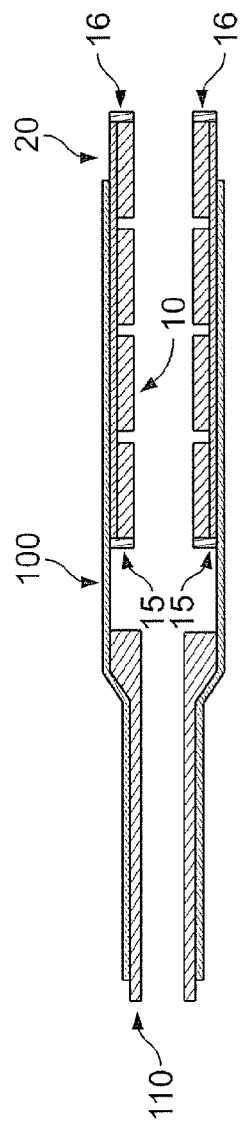

FIGS. 4A-4B illustrate loading of the inventive covered stent assembly into a catheter sheath 100 which acts to constrain the device from expansion. FIG. 4B depicts the proximally- and distally-joined covered stent assembly prepared as in FIGS. 1A-1D, substantially inserted into constraining catheter sheath 100.

FIGS. 5A-5B depict the steps in completing the delivery catheter assembly 120 after a pusher member 110 is pre-engaged within the catheter sheath 100, as assembly of the pusher member 110 after the covered stent assembly 25 is in the catheter sheath 100 would be impracticable. The covered stent assembly 25 may then be fully inserted into the catheter sheath 100 as shown in FIG. 5A, such as by using a pusher member similar to the pusher member 34, 32 shown in FIG. 1A, such that it abuts or is immediately adjacent to the pusher member 110. Once the covered stent assembly 25 is fully inserted into the catheter sheath 100 and positioned so that it abuts or is immediately adjacent to the pusher member 110, a guidewire shaft 122 is co-axially inserted through the central lumen of the covered stent assembly 25 and extends beyond the terminal end of the pusher member 110 and the catheter sheath 100. An atraumatic tip 130 is affixed to a distal end of the guidewire shaft 122 prior to insertion of the guidewire shaft 122. The atraumatic tip 130 is retracted into abutting relation with a distal end of the catheter sheath 100, thereby enclosing the covered stent assembly 25 within the catheter sheath 100.

In accordance with all aspects of the present invention, it is desirable that joining points 15 or 16 be formed by thermal methods, such as such as laser welding, plasma welding, resistance welding, and e-beam welding where both the stent 10 and the cover 20 are fabricated of metal or pseudometallic materials, preferably shape memory or superelastic materials, most preferably, nickel-titanium alloys. However, where the stent 10 and the cover 20 are dissimilar materials, such as nickel-titanium alloy and stainless steel, welding is generally not an acceptable method for joining nickel-titanium alloy to other materials, such as stainless steel, because brittle intermetallics are formed in the weld zone. Thus, where nickel-titanium alloy is to be joined to another biocompatible material, it is desirable to employ soldering, epoxies or adhesives to form the joining point 15. Alternatively, if welding dissimilar materials to nickel-titanium is desired, it is known to provide an interlayer material, such as tantalum, to minimize formation of brittle intermetallics during welding.

Figure 6A:
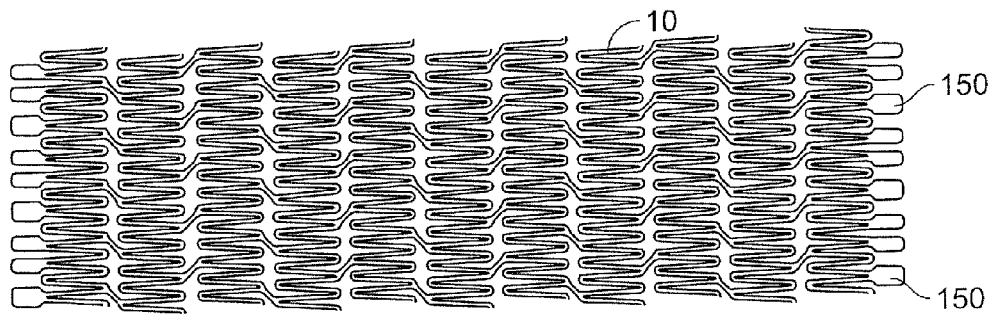
FIG. 6A is an expanded side view of the stent with proximal and distal junction points.
Figure 6B:
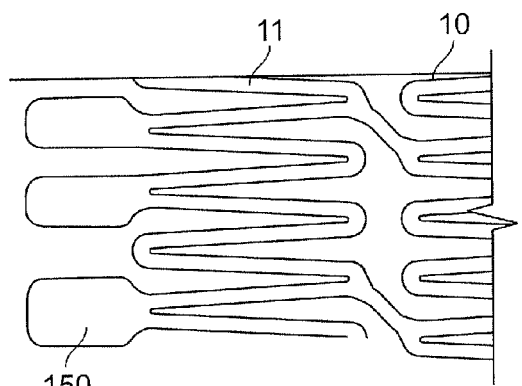
FIG. 6B is an enlarged side view of the stent with the proximal and distal junction points.
Figure 7:
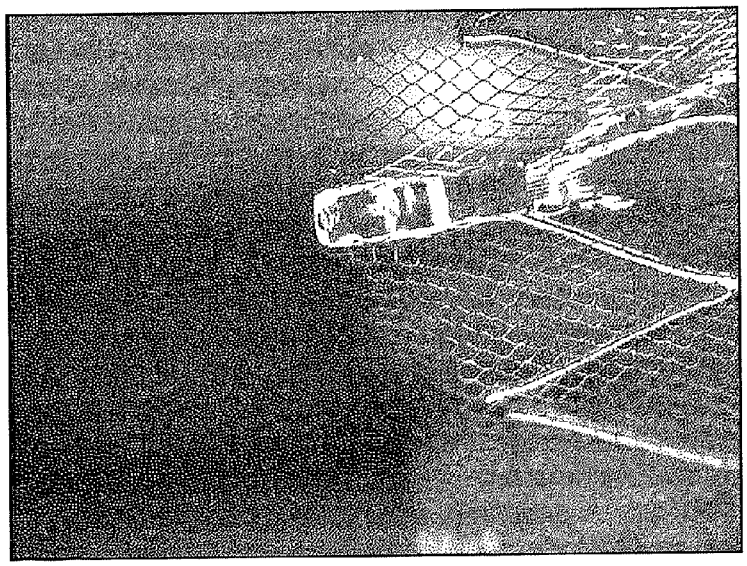
FIG. 7 is a photomicrograph illustrating a junction point of a stent welded to a cover.

Finally, in accordance with the best mode of the invention and the preferred embodiment thereof and as illustrated in FIGS. 6A and 6B, it is preferably to configure the stent 10 such that it has proximal and distal junction points 150 which provide a relatively larger, substantially planar surface area for creating the junction between the cover 20 and the stent 10. The junction points 150 may have a generally quadrilateral shape in the X-Y axis of either the luminal or abluminal surface of the stent 10, preferably has the same Z-axis wall thickness as the remaining portions of the stent 10, and have a slight curvature corresponding generally to the curvature of the tubular stent 10. FIG. 7 is a photomicrograph illustrating a junction point 150 of a stent 10 welded to a cover 20.

Alternatively, as described more fully in co-pending, commonly assigned patent application U.S. Publication No. US20040186554A1, entitled, "Endoluminal stent having mid-strut interconnecting members" or in co-pending, commonly assigned patent application U.S. Publication No. US20040098094A1, entitled "Implantable graft and methods of making same" the junction points 150 may be projections from terminal proximal and/or distal cylindrical members forming the tubular stent 10 (See, e.g., FIG. 1, element 11 in the '554 Publication or FIG. 27, elements 307 and 304a-e in the '094 Publication), each publication is hereby expressly incorporated by reference.

It is preferable, in accordance with the preferred embodiments of the invention, that when employing shape memory materials for both the stent and the cover, that the stent and the cover have different transition temperatures, such that the stent have its transition temperature below body temperature and diametrically expand when exposed to body temperature, while the cover preferably has a transition temperature above body temperature so that it undergoes detwinned martensitic plastic deformation due to expansion of the stent upon implanting into the body. Thus, it is preferred that the stent have an $A_f \leq 29°$ C.$\pm 3°$ C. and the cover have an have an $A_f$ between about 60 to 100° C. In this manner, the cover remains martensitic under all conditions which are likely to be encountered during manufacture, delivery and after being implanted in vivo. The stent, on the other hand, having an $A_f$ less than body temperature, will be constrained in the delivery catheter and readily expand during implantation in vivo, and readily expand the martensitic cover along with the radial expansion of the stent. Since the cover and the stent will be affixed to each other, it is desirable that the stent and the cover exhibit compatible degrees of foreshortening upon radial expansion of the resulting covered stent device.

The following examples are provided in order to illustrate the alternative embodiments of the invention, and are not intended to limit the scope of the invention.

Example 1

Preparation of a Proximally- and Distally-Joined Stent Assembly Using a Constant Outer Diameter Catheter Sheath A self-expanding shape memory nickel-titanium stent having a wall thickness of 127 μm, a 0.965 mm inner diameter ("ID") and 1.168 mm outer diameter ("OD") is loaded into a loading sheath of 1.194 mm ID and 1.295 mm OD of a loading/welding fixture, and a cover of 1.257 mm OD and 4.5 micron wall thickness is loaded over the loading sheath. The proximal end region of the cover is then welded to the proximal end region of the crimped stent.

The resulting proximally-joined covered stent assembly is slid into the distal end of a constraining tube having a 1.193 mm ID and 1.295 mm OD. The loading sheath of the loading/welding fixture is then retracted, the distal end region of the cover is welded to the distal end region of the stent, and the weld is passivated in a nitric acid solution.

The resulting proximally- and distally-joined covered stent assembly is then slid completely into the constant outer diameter catheter sheath. In one non-limiting embodiment of the present invention, this assembly is chilled in order to facilitate sliding. A pusher shaft of 0.031" ID and 0.051" OD is then inserted from the proximal end of the constant outer diameter catheter sheath, and a guidewire shaft of 0.018" ID and 0.027" OD comprising a proximal tip is inserted from the distal end of the constant outer diameter catheter sheath. Alternatively, the insertion of the guidewire shaft may precede the insertion of the pusher shaft.

Example 2

Preparation of a Proximally- and Distally-Joined Stent Assembly Using a Tapered Catheter Sheath A self-expanding shape memory stent having a wall thickness of 127 μm is crimped to an inner diameter ("ID") of 0.97 mm with an outer diameter ("OD") of 1.17 mm. The crimped stent is then loaded into a loading sheath having a 1.19 mm ID and 1.295 mm OD of a loading/welding fixture, and a cover of 1.257 mm OD and 4.5 micron wall thickness is loaded over the loading sheath. The proximal end region of the cover is then welded to the proximal end region of the crimped stent.

The resulting proximally-joined covered stent assembly is slid into a constraining tube having a 1.193 mm ID and a 1.295 mm OD. The loading sheath of the loading/welding fixture is then retracted, the distal end region of the cover is welded to the distal end region of the stent, and the weld is passivated in a nitric acid solution.

The resulting proximally- and distally-joined covered stent assembly is then slid completely into the distal end of a tapered catheter sheath having an ID of 1.397 mm and a 1.600 mm OD distally, tapered to 1.092 mm ID and 1.295 mm OD proximally, where this tapered catheter sheath contains a preloaded catheter pusher shaft of 0.737 mm ID and 1.295 mm OD distally, tapered to 0.737 mm ID and 0.991 mm OD proximally. In one non-limiting embodiment of the present invention, this assembly is chilled in order to facilitate sliding. A guidewire sheath of 0.457 mm ID and 0.686 mm OD and including an atraumatic tip is then inserted from the distal end of the tapered diameter catheter sheath.

While the present invention has been described with reference to its preferred embodiments, one of ordinary skill in the relevant art will understand that the present invention is not intended to be limited by these preferred embodiments, and is instead contemplated to include all embodiments consistent with the spirit and scope of the present invention as defined by the appended claims.

What is claimed is:

1. A method for preparing an implantable medical device, comprising:
   a) loading a stent into a lumen of a loading tube such that a first end region of the stent projects beyond a first terminal end of the loading tube;
   b) loading a cover over the terminal end of the loading tube and slidably engaging the cover onto the loading tube such that a first end region of the cover is in apposition with the first end region of the stent that projects beyond the first terminal end of the loading tube;
   c) joining the first end region of the cover to the first end region of the stent in a first join to form a covered stent assembly having the first join;
   d) loading the covered stent assembly having the first join into a restraining tube such that a second end region of the cover and a second end region of the stent project beyond a terminal end of the restraining tube; and
   e) joining the second end region of the cover to the second end region of the stent in a second join to form the implantable medical device.

2. The method of claim 1, wherein steps c) and e) further comprise the step of forming the first join and the second join by resistance welding.

3. The method of claim 2, further comprising the step of passivating the covered stent assembly.

4. The method of claim 1, further comprising the step of transferring the covered stent assembly from the restraining tube into a catheter sheath.

5. The method of claim 4, further comprising the steps of:
   a) disposing a pusher member within the catheter sheath prior to loading the implantable medical device into the catheter sheath;
   b) sliding the implantable medical device into the catheter sheath such that it is at least in adjacent proximity to the pusher member; and
   c) disposing a guidewire sheath through a central bore in the pusher member and through a central lumen of the implantable medical device.

6. The method of claim 4, wherein said catheter sheath further comprises a tapered catheter sheath.

7. The method of claim 6, further comprising:
   a) disposing a pusher member within the tapered catheter sheath prior to loading the implantable medical device into the catheter sheath;
   b) sliding the implantable medical device into the tapered catheter sheath such that it is at least in adjacent proximity to the pusher member; and
   c) disposing a guidewire sheath through a central bore in the pusher member and through a central lumen of the implantable medical device.

8. A method of joining a stent with a stent cover, comprising the steps of:
   a) loading the stent into a lumen of a loading tube such that a first end region of the stent projects beyond a first terminal end of the loading tube;
   b) loading the stent cover over the first terminal end of the loading tube and slidably engaging the stent cover onto the loading tube such that a first terminal end region of the stent cover is in apposition with the first end region of the stent that projects beyond the first terminal end of the loading tube;
   c) joining the first terminal end region of the stent cover to the first end region of the stent in a first join to form a covered stent assembly having the first join.

9. The method of claim 8, wherein step c) further comprises the step of forming the first join by resistance welding.

10. The method of claim 9, further comprising the step of passivating the first join.

* * * * *